United States Patent [19]

Miyake et al.

[11] Patent Number: 4,593,115
[45] Date of Patent: Jun. 3, 1986

[54] METHOD FOR PRODUCING 1-IODOALKYL ACYLATES

[75] Inventors: Akio Miyake; Masayoshi Yamaoka, both of Osaka, Japan

[73] Assignee: Takeda Chemical Industries, Ltd., Osaka, Japan

[21] Appl. No.: 673,944

[22] Filed: Nov. 21, 1984

[30] Foreign Application Priority Data

Nov. 25, 1983 [JP] Japan ................................ 58-222827

[51] Int. Cl.[4] .............................................. C07C 67/14
[52] U.S. Cl. ........................................ 560/1; 260/408;
560/105; 560/121; 560/123; 560/124; 560/238
[58] Field of Search ............................ 260/408, 544 Y;
560/226, 238, 1, 105, 121, 123, 124

[56] References Cited

FOREIGN PATENT DOCUMENTS 128911 6/1919 United Kingdom ................ 560/226
649508 11/1946 United Kingdom ................ 560/226

OTHER PUBLICATIONS

Noller, Chemistry of Organic Compounds, 2nd ed. 1957, W. B. Saunders Co., Philadelphia; pp.160–161.
Hilgetag and Weygand, Preparative Organic Chemistry 1972, John Wiley & Sons, New York; p. 247.
March, Advanced Organic Chemistry, 2nd ed., McGraw-Hill, New York; pp. 880–881.

Primary Examiner—Bernard Helfin
Attorney, Agent, or Firm—Antonelli, Terry & Wands

[57] ABSTRACT

An 1-Iodoalkyl acylate, which is useful as the raw material for esterification of cephalosporins, penicillins, etc. is prepared in a high degree of purity and in high yield by (1) allowing a carboxylic acid iodide to react with an aldehyde, or (2) allowing a carboxylic acid chloride to react with a salt of hydriodic acid and then allowing the resulting product to react with an aldehyde, or (3) by simultaneously allowing a carboxylic acid chloride, a salt of hydriodic acid and an aldehyde to react with one another.

8 Claims, No Drawings

METHOD FOR PRODUCING 1-IODOALKYL ACYLATES

This invention relates to 1-iodoalkyl acylates useful as materials for esterification of pharmaceutical compounds, such as cephalosporin or penicillin, having carboxyl or/and sulfo substituents in the molecule.

Hitherto, an 1-iodoalkyl acylate has been produced by the method which comprises reacting a carboxylic acid chloride with an aldehyde and then isolating thus obtained 1-chloroalkyl acylate, followed by reacting it with sodium iodide.

However, yield of the 1-iodoalkyl acylate produced by reacting 1-chloroalkyl acylate with sodium iodide is low and besides side reactions also occur. Therefore, this method is unsatisfactory in an industrial production.

The present inventors have made intensive researches in order to remove the above defects and found that a carboxylic acid iodide rapidly reacts with an aldehyde to produce an 1-iodoalkyl acylate in enhanced degree of purity and in increased yield.

Further investigations based on the above finding have led to completion of this invention.

The method of this invention has the advantage that an 1-iodoalkyl acylate is obtained in high purity and in high yield by reacting a carboxylic acid iodide with an aldehyde, with few byproducts being formed.

The object compound of this invention, namely, an 1-iodoalkyl acylate, is produced by allowing a carboxylic acid iodide to react with an aldehyde.

The examples of a carboxylic acid iodide used as one of the starting materials for the reaction of this invention include a straight-chain or branched aliphatic, alicyclic or aromatic carboxylic acid iodide which may optionally be substituted, such as a compound represented by the formula:

$$R_2COI \qquad (II)$$

wherein $R_2$ represents (1) a cycloalkyl group or (2) an alkyl group which may optionally be substituted by phenyl or a cycloalkyl group.

In the above formula, $R_2$ represents (1) a cycloalkyl group of 3 to 7 carbon atoms, such as cyclopropyl, cyclobutyl, cyclopentyl, cyclohexyl or cycloheptyl, or (2) a straight-chain or branched alkyl group of 1 to 10 carbon atoms, such as methyl, ethyl, n-propyl, isopropyl, n-butyl, isobutyl, t-butyl, n-pentyl, n-hexyl, 2-ethylbutyl, n-heptyl, n-octyl, n-nonyl or n-decyl, which may optionally be substituted by phenyl or a cycloalkyl group of 3 to 7 carbon atoms, such as cyclopropyl, cyclobutyl, cyclopentyl, cyclohexyl or cycloheptyl.

The examples of the aldehyde used as one of the starting materials for the reaction of this invention include a straight-chain or branched aliphatic, alicyclic, or aromatic aldehyde which may optionally be substituted, such as a compound represented by the formula:

$$R_1CHO \qquad (III)$$

wherein $R_1$ represents hydrogen, an alkyl group or a cycloalkyl group.

In the above formula, $R_1$ represents hydrogen, a straightchain or branched lower alkyl group of 1 to 6 carbon atoms, such as methyl, ethyl, n-propyl, isopropyl, n-butyl, isobutyl, t-butyl, n-pentyl, isopentyl, neopentyl, t-pentyl or n-hexyl, or a cycloalkyl group of 3 to 7 carbon atoms, such as cyclopropyl, cyclobutyl, cyclopentyl, cyclohexyl or cycloheptyl.

An 1-iodoalkyl acylate which is the object compound of this invention includes a compound represented by the formula:

$$\underset{\underset{\text{I-CH-O-C-R}_2}{|}}{R_1} \quad \underset{\|}{O} \qquad (I)$$

wherein the symbols have the same meanings as defined hereinbefore, when the above compounds (II) and (III) are used as starting materials.

In the reaction of this invention, the carboxylic acid iodide may be used in an amount of about 1 to 3, preferably about 1 to 1.5 moles per mole of the aldehyde.

This reaction may be carried out in the absence of a solvent, but may be carried out in a solvent which does not interfere with the reaction. As a suitable solvent, use is made of, for example, an aprotic organic solvent, such as nitriles e.g., acetonitrile; halogenated hydrocarbons, e.g., dichloromethane, chloroform or carbon tetrachloride; ketones, e.g., acetone or methyl ethyl ketone; amides, e.g., N,N-dimethylformamide; ethers, e.g., isopropyl ether, dioxane or tetrahydrofuran. Of these, preferred are nitriles, such as acetonitrile, ketones, such as acetone or methyl ethyl ketone, and amides, such as N,N-dimethylformamide. The reaction is carried out by adding the aldehyde to the carboxylic acid iodide or adding the carboxylic acid iodide to the aldehyde or simultaneously mixing them.

The reaction temperature is virtually optional but the reaction may be carried out at a temperature ranging from about −20° C. to room temperature, i.e. about 15° C., preferably about −20° C. to 5° C.

The reaction time is from about 5 minutes to 3 hours. The reaction may be performed with addition of a Lewis acid in a small amount, for example, about 0.01 to 0.05 moles per mole of the aldehyde as a starting material. The examples of suitable Lewis acid include, among others, zinc chloride, zinc bromide, zinc iodide, aluminum chloride and tin tetrachloride.

Furthermore, the object 1-iodoalkyl acylate may be produced by the first step of allowing a carboxylic acid chloride to react with a salt of hydriodic acid to produce a carboxylic acid iodide and then the second step of allowing the resulting product to react with an aldehyde.

The examples of the salt of hydriodic acid include among others, an alkali metal iodide, such as sodium iodide, potassium iodide; an alkaline earth metal iodide, such as calcium iodide, magnesium iodide or barium iodide; a transition metal iodide, such as zinc iodide or copper iodide; and a quaternary ammonium iodide, such as tetramethyl ammonium iodide. Of these, preferred is an alkali metal iodide.

The examples of carboxylic acid chloride include a straight-chain or branched aliphatic, alicyclic, or aromatic carboxylic acid chloride which may optionally be substituted, such as a compound represented by the formula:

$$R_2COCl \qquad (IV)$$

wherein $R_2$ has the same meaning as defined hereinbefore. The same aldehyde as mentioned above may be used as the starting aldehyde.

The first step of this reaction is a process of producing the carboxylic acid iodide by allowing the carboxylic acid chloride to react with the salt of hydriodic acid.

In the first step of this reaction, the salt of hydriodic acid is used usually in an amount of about 1 to 3, preferably about 1 to 1.5 equivalents to the carboxylic acid chloride.

This reaction is usually carried out in a solvent. As a suitable solvent, use is made of, for example, an aprotic organic solvent, such as nitriles, e.g., acetonitrile; halogenated hydrocarbons, e.g., dichloromethane, chloroform or carbon tetrachloride; ketones, e.g., acetone or methyl ethyl ketone; amides, e.g., N,N-dimethylformamide; or ethers, e.g., isopropyl ether, dioxane or tetrahydrofuran. Of these, preferred are acetonitrile, acetone and N,N-dimethylformamide.

In this reaction, the salt of hydriodic acid may be previously dissolved in said solvent, followed by adding the carboxylic acid chloride thereto, or the carboxylic acid chloride may be dissolved in said solvent, followed by adding thereto the salt of hydriodic acid, as such or as a solution in said solvent.

The reaction temperature is virtually optional, but the reaction may be carried out at about −20° C. to room temperature, i.e. about 15° C., preferably about −20° C. to 5° C.

The reaction time is about 5 minutes to 2 hours. The thus obtained carboxylic acid iodide may be used, as such, in the subsequent reaction or, if necessary, after it has been isolated and purified by per se known means, such as extraction with solvents, distillation, and/or distillation under reduced pressure.

The second step of this reaction is a process of producing the 1-iodoalkyl acylate by allowing the carboxylic acid iodide produced at the first step to react with the aldehyde. The aldehyde used in this reaction is used usually in an amount of about ⅓ to 1, preferably about 1/1.2 to 1 mole per mole of the carboxylic acid iodide.

This reaction is usually carried out in a solvent inert to the reaction. As a suitable solvent, use is made of, for example, an aprotic organic solvent, e.g., nitriles, such as acetonitrile; halogenated hydrocarbons, such as dichloromethane, chloroform or carbon tetrachloride; ketones, such as acetone or methyl ethyl ketone; amides, such as N,N-dimethylformamide; or ethers, such as isopropyl ether, dioxane or tetrahydrofuran. Of these, preferred are nitriles, such as acetonitrile, ketones, such as acetone or methyl ethyl ketone, and amides, such as N,N-dimethylformamide. The reaction temperature is virtually optional, and the reaction may be carried out at a temperature ranging from about −20° C. to room temperature, i.e. 15° C., preferably from about −20° C. to 5° C. The reaction time is about 5 minutes to 3 hours. This reaction may be carried out with addition of a Lewis acid. The Lewis acid is usually used in a small amount, e.g., in an amount of about 0.01 to 0.05 mole per mole of the aldehyde. The examples of the Lewis acid include, among others, zinc chloride, zinc bromide, zinc iodide, aluminum chloride and tin tetrachloride.

The object 1-iodoalkyl acylate may also be produced by simultaneously allowing the carboxylic acid chloride, the salt of hydriodic acid and the aldehyde to react with one another.

The proportion of the carboxylic acid chloride, the salt of hydriodic acid and the aldehyde is such that the carboxylic acid chloride is used in an amount of about 1 to 3, preferably about 1 to 1.2 moles per mole of the aldehyde and the salt of hydriodic acid is used in an amount of about 1 to 3, preferably about 1 to 1.5 moles equivalents to the carboxylic acid chloride.

This reaction is usually carried out in a solvent inert to the reaction. As the solvent, use is made of, for example, an aprotic organic solvent, such as nitriles, e.g., acetonitrile; halogenated hydrocarbons, e.g., dichloromethane, chloroform or carbon tetrachloride; ketones, e.g., acetone or methyl ethyl ketone; amides, e.g., N,N-dimethylformamide; or ethers, e.g., isopropyl ether, dioxane or tetrahydrofuran. Of these, preferred are nitriles, such as acetonitrile, ketones, such as acetone or methyl ethyl ketone and amides, such as N,N-dimethylformamide, etc.

The reaction may be carried out by dissolving the salt of hydriodic acid in said solvent and then adding thereto the aldehyde and the carboxylic acid chloride simultaneously or successively in the order of the aldehyde and then carboxylic acid chloride. In this case, the aldehyde and the carboxylic acid chloride may be used as solutions in said solvent.

The reaction temperature is virtually optional, but the reaction may be carried out at temperatures of from about −20° C. to room temperature, i.e. about 15° C., preferably from about −20° C. to 5° C. The reaction time is about 5 minutes to 3 hours. This reaction may be carried out with addition of a Lewis acid. The Lewis acid is usually used in a small amount, e.g. in an amount of about 0.01 to 0.05 mole per mole of the aldehyde. The examples of the Lewis acid include, among others, zinc chloride, zinc bromide, zinc iodide, aluminum chloride and tin tetrachloride.

The thus obtained 1-iodoalkyl acylate may be isolated and purified by per se known processes, such as extraction with a solvent e.g., n-hexane, petroleum ether, ethers, ethyl acetate, dichloromethane or chloroform, silica gel chromatography and/or distillation under reduced pressure.

The 1-iodoalkyl acylate may exist in the form of optical isomers due to the presence of one or more asymmetric carbon atom(s), and each such optical isomer is within the scope of this invention.

The 1-iodoalkyl acylate which is the object compound of this invention is used as a material for esterification of azetidinone compounds, cephalosporin compounds and penicillin compounds which have carboxyl and/or sulfo substituent(s) in the molecule.
inone, The esterification reactions of these azetidinone, cephalosporin and penicillin compounds may be carried out by per se known processes, for example, those disclosed in British Patent No. 1406113, Japanese Unexamined Published Patent Application No. 48790/1979. For example, esterification reaction of the carboxyl group at 4-position of 7β-[2-(2-aminothiazol-4-yl) acetamido]-3-[[[1-(2-dimethylaminoethyl)-1H-tetrazol-5-yl]thio]methyl]ceph-3-em-4-carboxylic acid [disclosed in Japanese Examined Published Patent Application No. 12913/1980; referred to as briefly "compound (V)" hereinafter], which is a cephalosporin compound, can be carried out by allowing the compound (V) to react with the 1-iodoalkyl acylate, e.g., the compound (I) in a solvent inert to the reaction.

Suitable solvents usable in this reaction are amides, ketones, nitriles and liquefied sulfurous anhydride. Concrete examples of these solvents include acetonitrile, N,N-dimethylformamide, N,N-dimethylacetamide, hexamethylphosphorotriamide, dichloromethane, chloroform, dimethyl sulfoxide, diethyl ether, dioxane, tetrahydrofuran, acetone, methyl ethyl ketone and dimethoxyethane. Of these, preferred are dimethylformamide, dimethylacetamide, hexamethylphosphorotriamide, acetone, acetonitrile and liquefied sulfurous anhydride.

The esterification reaction is generally effected at a temperature of from about −20° C. to 20° C. The reaction can be performed in the absence of a catalyst, but the catalyst, such as a phase transfer catalyst, e.g., 18-crown-6 may be used. When liquefied sulfurous anhydride is used as a solvent, the reaction is preferably carried out in the neighborhood of the boiling point (31 10° C.) of this solvent, namely, at −10° C. to −20° C. The time required for this reaction varies depending on the kinds of reactants and solvents, and is generally about 10 minutes to 6 hours.

The thus obtained azetidinone ester compounds, cephalosporin ester compounds and penicillin ester compounds or salts thereof, e.g., salts with inorganic acids such as hydrochloric acid, sulfuric acid or phosphoric acid, or organic acids, such as maleic acid, acetic acid, citric acid, succinic acid, tartaric acid, malic acid, malonic acid, fumaric acid, benzoic acid, mandelic acid, ascorbic acid or methanesulfonic acid can be isolated and purified by per se known processes e.g., crystallization, recrystallization and/or chromatography.

These azetidinone ester compounds, cephalosporin ester compounds and penicillin ester compounds are rapidly absorbed from the gastrointestinal tract when administered orally to give high concentration of the corresponding non-ester parent compound (V) in blood and are effective for the treatment of infections of human beings and mammals with bacteria (for example, gram-positive bacteria, such as *Staphylococcus aureus* and gram-negative bacteria, such as *Escherichia coli, Klebsiella pneumoniae, Proteus vulgaris, Proteus mirabilis* or *Proteus morganii*), for example, respiratory-organ infections, and urinary-tract infections caused by the bacteria.

The azetidinone ester compounds, cephalosporin ester compounds and penicillin ester compounds or salts thereof can be formulated into capsules, powders, fine granules, granules and tablets by per se conventional processes.

The azetidinone ester, cephalosporin ester and penicillin ester compounds or salts thereof can be orally administered at a daily dose level of 0.3 to 5 g, preferably 0.5 to 3 g per adult human in 3 to 4 divided doses per day.

The carboxylic acid chloride of the starting material can be produced by per se known processes, for example, the process disclosed in Karbin A. Buller and Donald E. Piason "Survey of Organic Synthesis" pages 859–893 (1970) published from Jone Willy and Son's Incorporated.

This invention is illustrated by the following non limiting examples.

The symbols used in the examples have the following meanings.

s: singlet, b-s: broad singlet, d: doublet, d.d: double doublet, t: triplet, q: quartet, ABq: AB type quartet and m: multiplet.

The term "%" means weight/weight % unless otherwise specified.

EXAMPLE 1

Production of cyclohexanecarbonyl iodide

In 80 ml of acetonitrile is dissolved 6 g of sodium iodide and, then, 5 g of cyclohexanecarbonyl chloride is added dropwise to the solution under ice-cooling. This mixture is stirred at 0° C. for 30 minutes. Then, insoluble matters are removed by filtration and the filtrate is concentrated under reduced pressure. To the residue is added 20 ml of petroleum ether and insoluble matters are removed by filtration and the filtrate is subjected to distillation under reduced pressure to obtain 5.0 g of cyclohexanecarbonyl iodide. Yield: 61%. B.p. 75°–80° C./5 mmHg [b.p. 103°–105° C./11 mmHg according to "Bull. Chem. Soc. Japan" 34, 480 (1961)].

EXAMPLE 2

Production of 1-iodoethyl cyclohexanecarboxylate

To 5.0 g of cyclohexanecarbonyl iodide is added 2 g of acetaldehyde while stirring under ice-cooling and the mixture is stirred for 30 minutes. Excess acetaldehyde is distilled off under reduced pressure to obtain 5.2 g of the titled compound. Yield: 88%.

$IR_{\nu max}^{liquid\ film} cm^{-1}$: 1760, 1740.

NMR (CDCl$_3$) δ: 1.10–1.80 (m, 10H), 2.20 (d, J=6Hz, 3H), 2.20–2.50 (m, 1H), 6.80 (q, J=6Hz, 1H).

EXAMPLE 3

Production of 1-iodo-2-methylpropyl cyclohexane-carboxylate

To 5.0 g of cyclohexanecarbonyl iodide is added 3.0 g of isobutyl aldehyde while stirring under ice-cooling and the mixture is stirred for 30 minutes. Excess isobutyl aldehyde is distilled off under reduced pressure to obtain 6.0 g of the titled compound. Yield: 92%.

$IR_{\nu max}^{liquid\ film} cm^{-1}$: 1760, 1740.

NMR (CDCl$_3$) δ: 1.00 (d, J=6Hz, 6H), 1.05–2.00 (m, 10H), 2.00–2.45 (m, 1H), 6.68 (d, J=2Hz, 1H).

EXAMPLE 4

Production of 1-iodoethyl cyclohexanecarboxylate

In 100 ml of acetonitrile is dissolved 15 g of sodium iodide and, then, 4.4 g of acetaldehyde is added to the solution. To the mixture is added dropwise 14.6 g of cyclohexanecarbonyl chloride while stirring under ice-cooling. After completion of the addition, the reaction mixture is stirred at 5° C. for 30 minutes, then poured into 200 ml of cold water and the mixture is extracted with 200 ml of n-hexane. The extract is successively washed with water, a 5% aqueous sodium thiosulfate solution and a 5% aqueous sodium bicarbonate solution in that order and, then, dried over anhydrous magnesium sulfate. The solvent is distilled off under reduced pressure to obtain 20 g of the titled compound (an oily product). Yield: 71%.

$IR_{\nu max}^{liquid\ film} cm^{-1}$: 1760, 1740.

NMR (CDCl$_3$) δ: 1.10–1.80 (m, 10H), 2.20 (d, J=6Hz, 3H), 2.20–2.50 (m, 1H), 6.80 (q, J=6Hz, 1H).

EXAMPLE 5

Production of 1-iodo-2-methylpropylcyclohexane-carboxylate

In 100 ml of acetonitrile is dissolved 15 g of sodium iodide. To this solution are added 200 mg of anhydrous zinc chloride and 8.0 g of isobutyl aldehyde. To the mixture is added dropwise 14.6 g of cyclohexanecarbonyl chloride while stirring under ice-cooling.

After completion of the addition, the reaction mixture is stirred at 5° C. for one hour, then poured into 200 ml of ice water and the mixture is extracted with 200 ml of n-hexane. The extract is successively washed with water, a 5% aqueous sodium thiosulfate solution and a 5% aqueous sodium bicarbonate solution in that order and dried over anhydrous magnesium sulfate. The solvent is distilled off under reduced pressure to obtain 24 g of the titled compound (an oily product). Yield: 80%.

$IR_{\nu max}^{liquid\ film}$ cm$^{-1}$:1760, 1740.

NMR (CDCl$_3$) δ:1.00 (d, J=6Hz, 6H), 1.05–2.00 (m, 10H), 2.00–2.45 (m, 1H), 6.68 (d, J=2Hz, 1H).

EXAMPLE 6

Production of 1-iodobutyl pentanoate

In 300 ml of acetonitrile is dissolved 45 g of sodium iodide and then to this solution are added dropwise simultaneously 25 g of n-butyl aldehyde and 36 g of valeryl chloride. The reaction mixture is stirred at 5° C. for 30 minutes, then poured into 600 ml of ice water and the mixture is extracted with 600 ml of n-hexane. The extract is successively washed with water, a 5% aqueous sodium thiosulfate solution and a 5% aqueous sodium bicarbonate solution in that order and dried over anhydrous magnesium sulfate. The solvent is distilled off under reduced pressure to obtain 65 g of the titled compound (an oily product). Yield: 76%.

$IR_{\nu max}^{liquid\ film}$ cm$^{-1}$:1760, 1740.

NMR (CDCl$_3$) δ:0.70–2.50 (m, 16H), 6.58 (t, J=6Hz, 1H).

EXAMPLE 7

Production of 1-iodobutyl 3-methylbutyrate

In 100 ml of acetonitrile is dissolved 15 g of sodium iodide. To this solution is added 8 g of n-butyl aldehyde and then to the mixture is added dropwise 12 g of isovaleryl chloride while stirring at −20° C., stirring at 0° C. for 30 minutes. The reaction mixture is poured into 200 ml of ice water and extracted with 200 ml of n-hexane. The extract is successively washed with water, a 5% aqueous sodium thiosulfate solution and a 5% aqueous sodium bicarbonate solution in that order and dried over anhydrous magnesium sulfate. The solvent is distilled off under reduced pressure to obtain 15 g of the titled compound (an oily product). Yield: 53%.

$IR_{\nu max}^{liquid\ film}$ cm$^{-1}$:1760.

NMR (CDCl$_3$) δ:0.80–1.20 (m, 9H), 1.2–1.60 (m, 4H), 2.00–2.24 (m, 2H), 6.80 (t, J=6Hz, 1H).

EXAMPLE 8

Production of 1-iodoethyl 3-ethylpentanoate

In 100 ml of acetonitrile is dissolved 15 g of sodium iodide. Thereafter, to the solution is added 4.4 g of acetaldehyde and then, to the mixture, is added dropwise 14.8 g of 3-ethylpentanoyl chloride while stirring under ice-cooling.

The reaction mixture is stirred at 5° C. for one hour, then poured into 200 ml of ice water and the mixture is extracted with 200 ml of n-hexane. The extract is successively washed with water, a 5% aqueous sodium thiosulfate solution and a 5% aqueous sodium bicarbonate solution in that order, and then dried over anhydrous magnesium sulfate. The solvent is distilled off under reduced pressure to obtain 26 g of the titled compound (an oily product). Yield: 87%.

$IR_{\nu max}^{liquid\ film}$ cm$^{-1}$:1760.

NMR (CDCl$_3$) δ:0.9 (t, J=6Hz, 6H), 1.30 (q, J=6Hz, 4H), 1.40–1.65 (m, 1H), 2.15 (d, J=6Hz, 3H), 2.30 (d, J=6Hz, 2H), 6.80 (q, J=6Hz, 1H).

EXAMPLE 9

Production of 1-iodo-2-methylpropyl 3-methylbutyrate

In 100 ml of acetonitrile is dissolved 15 g of sodium iodide. To this solution are added 100 mg of zinc chloride and 8 g of isobutyl aldehyde. To the mixture is added dropwise 12 g of isovaleryl chloride while stirring at −20° C. Then the reaction mixture is stirred at 0° C. for 30 minutes, poured into 200 ml of ice water and extracted with 200 ml of n-hexane. The extract is successively washed with water, a 5% aqueous sodium thiosulfate solution and a 5% aqueous sodium carbonate solution in that order and dried over anhydrous magnesium sulfate. The solvent is distilled off under reduced pressure to obtain 19 g of the titled compound (an oily product). Yield: 68%.

$IR_{\nu max}^{liquid\ film}$ cm$^{-1}$:1760, 1740.

NMR (CDCl$_3$) δ:0.9 (d, J=8Hz, 12 H), 1.20–1.60 (m, 2H), 2.20 (d, J=6Hz, 2H), 6.82 (d, J=6Hz, 1H).

EXAMPLES 10 to 23

The compounds of the formula (I) obtained in the same manner as in Example 3 are shown in Table 1.

$$\underset{I-CH-O-C-R_2}{\overset{R_1\quad\ O}{|\quad\ \ \ \|}} \qquad (I)$$

TABLE 1

| Example No. | R$_1$ | R$_2$ | Yield (%) | $IR\nu_{max}^{liquid\ film}$ cm$^{-1}$ |
|---|---|---|---|---|
| 10 | —CH$_3$ | cyclopentyl (—CH(CH$_2$CH$_2$CH$_2$CH$_2$)) | 62 | 1765, 1755 |
| 11 | —CH$_3$ | cyclobutyl (—CH(CH$_2$CH$_2$)(CH$_2$CH$_2$)) | 77 | 1760, 1740 |
| 12 | —CH$_3$ | cyclopropyl (—CH(CH$_2$)(CH$_2$)) | 70 | 1755, 1750 |

TABLE 1-continued

| Example No. | R₁ | R₂ | Yield (%) | IR$\nu_{max}^{liquid\ film}$ cm$^{-1}$ |
|---|---|---|---|---|
| 13 | —CH₃ | —CH₂—CH(CH₂CH₂)₂CH (cyclohexyl-methyl) | 67 | 1760, 1755 |
| 14 | —CH₃ | —CH₃ | 70 | 1760, 1750 |
| 15 | —CH₃ | —CH₂CH(CH₃)(C₂H₅) | 81 | 1760, 1755 |
| 16 | —C₂H₅ | —CH(CH₂CH₂)₂CH₂ (cyclohexyl) | 76 | 1760, 1740 |
| 17 | —CH₂CH₂CH₃ | —CH(CH₂CH₂)₂CH₂ (cyclohexyl) | 79 | 1760, 1750 |
| 18 | —CH(CH₃)₂ | —CH₂—C₆H₅ | 85 | 1760, 1755 |
| 19 | —CH₂CH₂CH₂CH₃ | —CH₂—C₆H₅ | 88 | 1760, 1755 |
| 20 | —C(CH₃)₃ | —CH₃ | 47 | 1765, 1760 |
| 21 | —CH(CH₂CH₂)₂CH₂ (cyclohexyl) | —CH(CH₂CH₂)₂CH₂ (cyclohexyl) | 80 | 1760, 1750 |
| 22 | —CH(CH₂CH₂)₂CH₂ (cyclohexyl) | —CH₂CH₂CH₃ | 88 | 1760, 1740 |
| 23 | —CH(CH₂CH₂)₂CH₂ (cyclohexyl) | —CH₂CH₂CH₂CH₃ | 75 | 1755, 1740 |

EXAMPLE 24

Production of 1-iodoethyl cyclohexanoate

In 200 ml of acetonitrile is suspended 22 g of zinc iodide. To this suspension is added 4.4 g of acetaldehyde. To the mixture is added dropwise 14.6 g of cyclohexanecarbonyl chloride while stirring under ice-cooling. After completion of the addition, the mixture is stirred at room temperature for 2 hours, then poured into 200 ml of ice water and the mixture is extracted with 200 ml of n-hexane. The extract is successively washed with water, a 5% aqueous sodium thiosulfate solution and a 5% aqueous sodium bicarbonate solution in that order and dried over anhydrous magnesium sulfate. The solvent is distilled off under reduced pressure to obtain 18 g of the titled compound. Yield 64%.

The IR and NMR spectra of the thus obtained compound are confirmed to be identical with those of the compound obtained in Example 4.

EXAMPLE 25

Production of 1-iodoethyl cyclohexanecarboxylate

In 100 ml of acetonitrile is dissolved 14 g of tetraethylammonium iodide. To this solution are added simultaneously 7.3 g of cyclohexanecarbonyl chloride and 2.3 g of acetaldehyde. The reaction mixture is stirred at room temperature for 4 hours. To the reaction mixture is added 200 ml of ice water, and the mixture is extracted with 200 ml of n-hexane. The extract is successively washed with water, a 5% aqueous sodium thiosulfate solution and a 5% aqueous sodium carbonate solution and dried over anhydrous magnesium sulfate. The solvent is distilled off under reduced pressure to obtain 5.0 g of the titled compound. Yield: 36%.

The IR and NMR spectra of the resultant compound are confirmed to be identical with those of the compound obtained in Example 4.

EXAMPLE 26

Production of pivaloyloxymethyl iodide

To a mixture of 4.5 g of sodium iodide and 1.0 g of trioxane in 30 ml of acetonitrile, 3.6 g of pivaloyl chloride is added dropwise while stirring under ice-cooling. The mixture is stirred for 60 minutes at 60° C. Fifty ml of n-hexane and 50 ml of water are added to the reaction mixture and the aqueous layer is discarded. The organic layer is washed with water once and dried over magnesium sulfate. Evaporation of the solvent gives 4.8 g of the titled compound as an oil. Yield: 66%.

NMR (CDCl$_3$) δ:1.18 (s, 9H), 5.88 (s,2H).

REFERENCE EXAMPLE 1

Production of 1-cyclohexylcarbonyloxy-2-methylpropyl 7β-[2-(2-aminothiazol-4-yl)acetamido]3-[[[1-(2-dimethylaminoethyl)-1H-tetrazol-5-yl]thio]methyl]ceph-3-em-4-carboxylate.dihydrochloride In 120 ml of dimethylacetamide is dissolved 6.0 g of potassium 7β-[2-(2-aminothiazol-4-yl)acetamido]- 3-[[[1-(2-dimethylaminoethyl)-1H-tetrazol-5-yl]thio]methyl]ceph-3-em-4-carboxylate and this solution is cooled to −5° C. While stirring, 12.4 g of 1-iodo-2-methylpropyl cyclohexanecarboxylate is added to the solution at one stroke, followed by stirring for 10 minutes.

To the reaction mixture is added 70 ml of 2N-hydrogen chloride-ether solution and further 300 ml of ether. The ether layer is removed and the residue is dissolved in 50 ml of 1N hydrochloric acid. Then, the solution is chromatographed on a column of XA-DII® resin (manufactured by Rohm and Haas Co., U.S.A.) and developed with water-acetonitrile (3:1 volume/volume). The fractions containing the desired compound are collected, subjected to concentration under reduced pressure to remove the solvent and then lyophilized to obtain 6.0 g of the titled compound as colorless powder.

IR$_{vmax}^{KBr}$cm$^{-1}$:1780, 1750, 1680.

NMR (d$_6$ - DMSO) δ:0.90 (d, J=8Hz, 6H), 1.0-2.0 (m, 11H), 2:20-2.40 (m, 1H), 2,80 (s, 6H), 3.60 (s, 2H), 3.60-3.70 (m, 2H), 4.26 (t, J=6Hz, 2H), 5.10 (d, J=4.5Hz, 1H), 5.70 (d.d, J=4.5Hz and 6Hz, 1H), 6.60 (s, 1H), 6.63 (d, J=4.5Hz, 1H), 9.0-9.6 (b.s, 1H), 9.20 (d, J=6Hz, 1H).

Elemental analysis: for C$_{29}$H$_{41}$N$_9$O$_6$S$_3$. 2HCl.2H$_2$O: Calcd.(%): C 42.64; H 5.81; N 15.44: Found (%): C 42.80; H 5.92; N 15.59:

REFERENCE EXAMPLE 2

Production of 1-(3-ethyl)pentanoyloxyethyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride The titled compound is obtained in the same manner as in Reference Example 1 from potassium 7β-[2-(2-aminothiazol-4-yl)acetamido]-3-[[[1-(2-dimethyl-aminoethyl)-1H-tetrazol-5-yl]thio]methyl]ceph-3-em-4-carboxylate and 1-iodoethyl 3-ethyl pentanoate.

IR$_{vmax}^{Nujol}$cm$^{-1}$:1785, 1755, 1685.

NMR (D$_2$O) δ:1.07 (t, J=7Hz, 6H), 1.45-2.17 (m, 11H), 2.60 (t, J=6Hz, 2H), 3.30 (s, 8H), 3.8-4.3 (m, 5H), 4.65 (b.s, 2H), 5.20 (t, J=6Hz, 2H), 5.45(d, J=4.5Hz, 1H), 5.92 (d, J=4.5Hz, 1H), 7.00 (s, 1H), 7.20 (q, J=6Hz, 1H).

Elemental analysis: for C$_{27}$H$_{39}$N$_9$O$_6$S$_3$.2HCl.2H$_2$O: Calcd. (%): C 41.01; H 5.74; N 15.94: Found (%): C 40.69; H 5.92; N 15.78:

REFERENCE EXAMPLE 3

Production of 1-(3-methyl)butyryloxy-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate.dihydrochloride The titled compound is obtained in the same manner as in Reference Example 1.

IR$_{vmax}^{KBr}$cm$^{-1}$: 1780, 1750, 1680.

NMR (d$_6$-DMSO) δ: 0.90 (d, J=7.5Hz, 6H), 0.93 (d, J=7.5Hz, 6H), 1.90-2.20 (m, 4H), 2.85 (s, 6H), 3.60 (s, 2H), 3.65-3.90 (m, 2H), 4.30 (s, 2H), 4.76 (t, J=6Hz, 2H), 5.10 (d, J=4.5Hz, 1H), 5.60-5.80 (m, 1H), 6.63 (s, 1H), 6.63-6.76 (m, 1H), 8.90-9.50 (b.s, 1H), 9.20 (d, J=9Hz, 1H).

Elemental analysis: for C$_{27}$H$_{39}$N$_9$O$_6$S$_3$.2HCl.9/2-H$_2$O: Calcd. (%): C 38.80; H 6.03; N 15.09: Found (%): C 38.72; H 5.62; N 15.08:

For comparison, production methods of the compound (I) according to known methods e.g. described in EP-93548A are shown in Experimental Examples 1 to 5.

EXPERIMENTAL EXAMPLE 1

Production of 1-iodoethyl cyclohexanecarboxylate (a) A mixture of 66.0 g of cyclohexanecarbonyl chloride and 0.3 g of anhydrous zinc chloride is cooled to −10° C. To the mixture, 30.2 ml of acetaldehyde is added at the temperature below −5° C. while stirring, and the reaction mixture is stirred at −5° C.-0° C. for 2 hours. Then, the reaction mixture is mounted on a silica gel (50 g) column and the column is eluted with 700 ml of n-hexane. After evaporation of the solvent under reduced pressure, the residue is subjected to distillation in vacuo to give 73.5 g of 1-chloroethyl cyclohexanecarboxylate. B.p.: 60°-63° C./2 mmHg. Yield: 85.6%.

(b) A mixture of 134.9 g of sodium iodide in 810 ml of acetonitrile is heated to 40° C. To the mixture, 57.2 g of 1-chloroethyl cyclohexanecarboxylate obtained in above (a) is added and the mixture is stirred at the same temperature for 30 minutes. Then, the reaction mixture is poured into 2.4 l of ice-water and the resulting mixture is extracted with each 400 ml of n-hexane twice. The extracts are combined, washed with 5% aqueous sodium thiosulfate (250 ml×2), water (300 ml×2), successively, and dried over sodium sulfate. The solvent is evaporated to give 49.1 g of an oil in which the content of 1-iodoethyl cyclohexanecarboxylate (the content is calculated on the basis of the NMR-spectrum analysis of the product. This method is used in the following Experimental Examples) is about 60%.

The yield of 1-iodoethyl cyclohexanecarboxylate is 35% (overall yield from cyclohexanecarbonyl chloride: 30%).

EXPERIMENTAL EXAMPLE 2

Production of 1-iodoethyl 3-methylvalerate (a) 3-Methylvaleryl chloride (71.5 g), anhydrous zinc chloride (0.14 g) and acetaldehyde (31 ml) are allowed to react with each other in the same manner as in Experimental Example 1-(a) to give 77.4 g (81.6% yield) of 1-chloroethyl 3-methylvalerate. B.p.: 90°–97° C./35 mmHg.

(b) The 1-chloroethyl 3-methylvalerate (2.0 g) and sodium iodide (6.4 g) are allowed to react with each other in 60 ml of acetonitrile at 45° C.–47° C. for 30 minutes and the reaction mixture is worked up as in Experimental Example 1-(b) to give 1.7 g of an oily product in which the content of 1-iodoethyl 3-methylvalerate is 60%.

The yield of 1-iodoethyl 3-methylvalerate is 34% (overall yield from 3-methylvaleryl chloride: 27.7%).

EXPERIMENTAL EXAMPLE 3

Production of 1-iodoethyl 3-ethylpentanoate (a) In the same manner as in Experimental Example 1-(a), 26.2 g (Yield:52.7%) of 1-chloroethyl 3-ethylpentanoate is obtained from 38.3 g of 3-ethylpentanoyl chloride, 0.2 g of anhydrous zinc chloride and 17.3 ml of acetaldehyde. B.p.: 100°–102° C./45 mmHg.

(b) 1-Chloroethyl 3-ethylpentanoate (1.93 g) and sodium iodide (3.0 g) are allowed to react with each other in 18 ml of acetonitrile at 40° C. for 30 minutes and the reaction mixture is treated as in Experimental Example 1-(b) to give 2.3 g of an oil in which the content of 1-iodoethyl 3-ethylpentanoate is 60%.

The yield of 1-iodoethyl 3-ethylpentanoate is 49% (overall yield from 3-ethylpentanoyl chloride: 25.8%).

EXPERIMENTAL EXAMPLE 4

Production of 1-iodoethyl 2-cyclohexylacetate (a) In the same manner as in Experimental Example 1-(a), 54.8 g (Yield: 83.7%) of 1-chloroethyl-2-cyclohexylacetate is obtained from 51.3 g of 2-cyclohexylacetyl chloride, 0.2 g of anhydrous zinc chloride and 18 ml of acetaldehyde. B.p.: 77°–79° C./4 mmHg.

(b) The 1-chloroethyl 2-cyclohexylacetyl chloride (54.8 g) is allowed to react with 160.7 g of sodium iodide in 800 ml of acetonitrile at 40° C. for 30 minutes, and the reaction mixture is worked up as in Experimental Example 1-(b) to give 52.9 g of an oil in which the content of 1-iodoethyl 2-cyclohexylacetate is 50%.

The yield of 1-iodoethyl 2-cyclohexylacetate is 33% (overall yield from 2-cyclohexylacetyl chloride: 27.6%).

EXPERIMENTAL EXAMPLE 5

Production of 1-iodo-2-methylpropyl cyclohexane-carboxylate (a) In the same manner as in Experimental Example 1-(a), 281 g (Yield: 75.4%) of 1-chloro-2-methylpropyl cyclohexanecarboxylate is obtained from 250 g of cyclohexylcarbonyl chloride, 1.2 g of anhydrous zinc chloride and 150 g of isobutylaldehyde. B.p.: 120°–123° C./18 mmHg.

(b) 1-Chloro-2-methylpropyl cyclohexanecarboxylate (50.3 g) and sodium iodide (68.9 g) are allowed to react with each other. in 395 ml of acetonitrile at 48° C.–50° C. for 2 hours, and the reaction mixture is treated as in Experimental Example 1-(b) to give 38.5 g of an oil in which the content of 1-iodo-2-methylpropyl cyclohexanecarboxylate is 60%.

The yield of 1-iodo-2-methylpropyl cyclohexanecarboxylate is 32.4% (overall yield from cyclohexylcarbonyl chloride: 24.4%).

Comparison of yield of the compound (I) obtained according to the method of this invention with that obtained according to the known method is shown below.

$$I-\underset{\underset{R_1}{|}}{CH}-O-\underset{\underset{}{\overset{O}{\|}}}{C}-R_2 \qquad (I)$$

| $R_1$ | $R_2$ | The method of this invention | | The known method | |
|---|---|---|---|---|---|
| | | Yield (%) of (I) | Example No. | Yield (%) of (I) | Experimental Example No. |
| $CH_3-$ | $C_2H_5$\\<br>  $CHCH_2-$\\ $CH_3$/ | 81 | 15 | 27.7 | 2 |
| $CH_3-$ | $CH_2\underset{CH_2CH_2}{\overset{CH_2CH_2}{\diagup\diagdown}}CH-$ | 71 | 4 | 30.0 | 1 |
| $CH_3-$ | $C_2H_5$\\<br>  $CHCH_2-$\\ $C_2H_5$/ | 87 | 8 | 25.8 | 3 |
| $CH_3-$ | $CH_2\underset{CH_2CH_2}{\overset{CH_2CH_2}{\diagup\diagdown}}CHCH_2-$ | 67 | 13 | 27.6 | 4 |
| $CH_3$\\$CH-$\\$CH_3$/ | $CH_2\underset{CH_2CH_2}{\overset{CH_2CH_2}{\diagup\diagdown}}CH-$ | 92 | 3 | 24.4 | 5 |

We claim:

1. A method for producing an 1-iodoalkyl acylate of the formula:

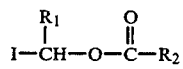

wherein $R_1$ hydrogen, a straight-chain or branched alkyl group of 1 to 6 carbon atoms, or a cycloalkyl group of 3 to 7 carbon atoms and $R_2$ is a cycloalkyl group of 3 to 7 carbon atoms, a straight-chain or branched alkyl group of 1 to 10 carbon atoms, which is non-substituted or substituted by phenyl or a cycloalkyl group of 3 to 7 carbon atoms, which comprises reacting a compound of the formula:

$$R_1CHO$$

wherein $R_1$ has the same meaning as defined above; a compound of the formula:

$$R_2COCl$$

wherein $R_2$ has the same meaning as defined above; and sodium iodide in a reaction mixture.

2. A method according to claim 1, wherein $R_1$ is methyl or isopropyl, and $R_2$ is cyclohexyl or 2-methylpropyl.

3. A method according to claim 1, wherein the compound of the formula: $R_2COCl$ is used in an amount of about 1 to 3 moles per mole of the compound of the formula: $R_1CHO$ and sodium iodide is used in an amount of about 1 to 3 mole equivalents to the compound of the formula: $R_2COCl$.

4. A method according to claim 1, wherein the reactions are carried out in a solvent inert to the reactions.

5. A method according to claim 4, wherein the reactions are carried out by initially dissolving sodium iodide in the solvent and then adding the compound of the formula: $R_1CHO$ and the compound of the formula: $R_2COCl$ simultaneously or successively in the order of the compound of the formula: $R_1CHO$ and then the compound of the formula: $R_2COCl$.

6. A method according to claim 5, wherein the reactions are carried out at temperatures of from about $-20°$ C. to about $15°$ C. for a period of from 5 minutes to 3 hours.

7. A method according to claim 1, wherein the reactions are carried out in the presence of a Lewis acid in an amount of about 0.01 to 0.05 mole per mole of $R_1CHO$.

8. A method according to claim 1, wherein the compound of the formula: $R_2COCl$, the compound of the formula: $R_1CHO$ and sodium iodide react simultaneously with one another.

* * * * *